United States Patent
Andreux et al.

(10) Patent No.: US 10,695,320 B2
(45) Date of Patent: Jun. 30, 2020

(54) COMPOSITIONS COMPRISING UROLITHIN COMPOUNDS

(71) Applicant: Amazentis SA, Ecublens (CH)

(72) Inventors: Penelope Andreux, Eclepens (CH); Christopher Rinsch, Morges (CH); William Blanco-Bose, Lausanne (CH)

(73) Assignee: Amazentis SA, Ecublens (CH)

( * ) Notice: Subject to any disclaimer, the term of this patent is extended or adjusted under 35 U.S.C. 154(b) by 0 days.

(21) Appl. No.: 15/757,293

(22) PCT Filed: Aug. 26, 2016

(86) PCT No.: PCT/EP2016/070255
§ 371 (c)(1),
(2) Date: Mar. 2, 2018

(87) PCT Pub. No.: WO2017/036992
PCT Pub. Date: Mar. 9, 2017

(65) Prior Publication Data
US 2018/0243261 A1    Aug. 30, 2018

(30) Foreign Application Priority Data

Aug. 28, 2015 (GB) ................................. 15155387.7

(51) Int. Cl.
| | |
|---|---|
| *A61K 31/366* | (2006.01) |
| *A61K 47/14* | (2017.01) |
| *A61K 47/24* | (2006.01) |
| *C07D 311/80* | (2006.01) |
| *A61K 9/08* | (2006.01) |
| *A61P 21/00* | (2006.01) |
| *A61K 9/50* | (2006.01) |

(52) U.S. Cl.
CPC .............. *A61K 31/366* (2013.01); *A61K 9/08* (2013.01); *A61K 9/50* (2013.01); *A61K 47/14* (2013.01); *A61K 47/24* (2013.01); *A61P 21/00* (2018.01); *C07D 311/80* (2013.01)

(58) Field of Classification Search
CPC .................................................... A61K 31/366
See application file for complete search history.

(56) References Cited

U.S. PATENT DOCUMENTS

| | | | |
|---|---|---|---|
| 8,894,993 B2 * | 11/2014 | Ghosal | ....................... A23L 2/52 424/94.1 |
| 2002/0018772 A1 | 2/2002 | Udell et al. | |
| 2005/0282781 A1 * | 12/2005 | Ghosal | ................. A61K 31/366 514/80 |
| 2014/0079729 A1 * | 3/2014 | Kalidindi | ........... A61K 38/1709 424/195.18 |

FOREIGN PATENT DOCUMENTS

| | | | | |
|---|---|---|---|---|
| WO | WO-2015/097231 A1 | | 7/2015 | |
| WO | WO-2015097231 A1 * | | 7/2015 | ........... C07D 311/80 |

OTHER PUBLICATIONS

Grob, Muscular Disease, Bull N Y Acad Med. Dec. 1961; 37(12): 809-834.*
International Search Report and Written Opinion for International Application No. PCT/EP2016/070255 dated Dec. 19, 2016.
Seeram, "Pharmacokinetics and tissue disposition of urolithin A, an ellagitannin-derived metabolite, in mice," The FASEB J, 21(6):A1081 (2007).

* cited by examiner

*Primary Examiner* — Svetlana M Ivanova
(74) *Attorney, Agent, or Firm* — Dana M. Gordon; Foley Hoag LLP (57) ABSTRACT

The invention provides compositions comprising a medium chain triglyceride and a urolithin. The invention also provides uses and methods associated with, or making use of the compositions, such as a medicament, dietary supplement, functional food or medical food and in the treatment and/or prophylaxis of a muscle-related pathological condition.

9 Claims, 2 Drawing Sheets

COMPOSITIONS COMPRISING UROLITHIN COMPOUNDS

The current invention relates to nutritional and medical formulations of urolithins and medium chain triglycerides.

BACKGROUND

Urolithins have potent effects on the improvement of a number of health conditions, and they have been shown to be highly biologically active in vitro and in vivo. Urolithins have been proposed as treatments of a variety of conditions including conditions related to inadequate mitochondrial activity, including obesity, memory decline, reduced metabolic rate, metabolic syndrome, diabetes mellitus, cardiovascular disease, hyperlipidemia, neurodegenerative diseases, cognitive disorder, mood disorder, stress, anxiety disorder, fatty liver disease (for example, NAFLD or NASH) and for improving liver function and weight management. In particular, urolithins have been shown to have beneficial effects in the enhancement of muscle function.

Low muscle mass or poor muscle performance are characteristics of many diseases and conditions. Muscle-related pathological conditions include myopathies, neuromuscular diseases, such as Duchenne muscular dystrophy, acute sarcopenia, for example muscle atrophy and/or cachexia, for example associated with burns, bed rest, limb immobilization, or major thoracic, abdominal, neck and/or orthopedic surgery. Age-related muscle-loss is an especially prevalent condition. Cachexia due to prolonged immobilization or other diseases, for example cancer, are other conditions that are often characterised by poor muscle performance.

Good muscle performance is important for effective living at all stages of life in healthy individuals as well as in those individuals suffering from a disease, especially the elderly. Improved muscle performance is also of particular interest to athletes. For example an increase in muscular contraction strength, increase in amplitude of muscle contraction, or shortening of muscle reaction time between stimulation and contraction are all of benefit to individuals, especially athletes.

In severe cases of muscular atrophy, an anabolic steroid such as methandrostenolone is administered to patients to assist in the curative process. Such drugs can have numerous side-effects so their long-term use is preferably avoided.

Urolithin compounds have properties that render them useful in the treatment and prophylaxis of various conditions, including in the enhancement of muscle function. However, in simple suspension in saline, the urolithins display an unfavourable pharmacokinetic profile with a delayed second increase in blood level some time after the initial peak, rendering such suspensions difficult for administration.

Multiple peaking of an orally administered compound in the blood fluid, with two or more peaks in concentration over time can be due to a number of factors, including: (i) formulation, such as the choice of excipient; (ii) the physiology of the gastrointestinal tract itself, including pH and components of the bile, which is regulated by hormonal and dietary factors; (iii) biochemical differences in the regional areas of the gastrointestinal tract that can lead to the creation of windows for absorption and hence multiple peaking; and (iv) enterohepatic recycling. When administering bioactive compounds orally, it is preferable that the plasma concentration of the compound presents as a single peak rather than with a multiple peak profile. Formulations that permit a single peak of an active compound following oral dosing facilitate the optimization of the dose to be administered as well as the frequency of administration as compared to formulations that lead to multiple peaks in the blood fluid. Consequently, formulations that yield a single peak are desirable and facilitate establishing a therapeutic dosing window within which a compound can exert its health benefits in mammals.

In addition to the undesirable pharmacokinetic properties of the simple saline suspension, in many settings, the compounds also suffer from a limited bioavailability. There is thus a need for formulations of urolithins that have both an acceptable pharmacokinetic profile, and improved bioavailability.

SUMMARY OF THE INVENTION

The present invention provides a composition comprising:
a) a medium-chain triglyceride; and
b) a compound of formula (I) or a salt thereof:

wherein:
A, B, C and D are each independently selected from H and OH;
W, X and Y are each independently selected from H and OH; and
Z is selected from H and OH.

Compounds of Formula (I) are members of the urolithin family; in particular, the compound of Formula (I) may be Urolithin A. Urolithin A in a composition of medium-chain triglyceride and Urolithin A has surprisingly been found to have an improved bioavailability and pharmacokinetic profile as compared with Urolithin A on its own in simple saline suspension. The composition of the invention is thus useful in the improvement of general health, and in the management of general health in healthy individuals as well as in the treatment and prophylaxis of various diseases and conditions, in particular conditions characterised by inadequate mitochondrial activity. In particular, the composition finds use in the treatment and management of healthy individuals who would benefit from improved muscle function, including individuals having impaired physical performance, impaired endurance capacity, and impaired muscle function. The composition also finds use in the treatment, prevention or management of diseases and conditions characterised by low muscle mass or poor muscle performance, and in the enhancement of muscle growth and/or muscle performance. It is also useful in maintaining muscle function.

The invention further provides a composition of the invention for use in the treatment of a variety of conditions, including conditions related to inadequate mitochondrial activity, including obesity, reduced metabolic rate, metabolic syndrome, diabetes mellitus, cardiovascular disease, hyperlipidemia, memory decline, neurodegenerative diseases, cognitive disorder, mood disorder, stress, and anxiety disorder, fatty liver disease (for example, NAFLD or NASH), and for improving liver function and weight management. In particular, the invention provides a composition for use in the treatment of muscle-related pathological conditions. The invention also provides a method of treating a muscle-related pathological condition in a subject comprising administering to the subject an effective amount of a composition of the invention. The invention provides a composition of the invention for use in enhancing muscle performance. The invention also provides a method of enhancing muscle performance by administering to a subject an effective amount of a composition of the invention.

The invention further provides a compound of Formula (I) or a salt thereof having $D_{50}$ size in the range 0.5 to 50 µm and a $D_{90}$ size in the range 5 to 100 µm. Preferably, the compound or salt has a $D_{90}$ size in the range 8.2 to 16.0 µm, a $D_{50}$ size in the range 2.8 to 5.5 µm and a $D_{10}$ size in the range 0.5 to 1.0 µm. It has been found that the compounds of the invention with those particle sizes have good dispersion and dissolution properties, and enhanced bioavailability.

DETAILED DESCRIPTION

As described above, the invention provides a composition comprising a medium-chain triglyceride and a urolithin.

The medium-chain triglyceride typically makes up at least 1% w/w of the composition of the invention, for example at least 5% w/w, for example at least 10% w/w, for example at least 15% w/w. The medium-chain triglyceride preferably makes up 20% w/w or more of the composition, for example 25% w/w or more by weight, for example 30% w/w or more by weight of the composition. For example the medium-chain triglyceride may make up 1-40% w/w of the composition, 2-40% w/w of the composition, 5-40% w/w of the composition; 10-40% w/w of the composition; 1-99% w/w of the composition, 5-99% w/w of the composition, 10-99% w/w of the composition, 20-99% w/w of the composition, 5-90% w/w of the composition, 10-90% w/w of the composition, for example 20-90% w/w of the composition, 20-80% w/w of the composition for example, 30-80% w/w of the composition, for example 30-70% w/w of the composition, for example 30-60% w/w of the composition, for example 30-50% w/w of the composition, for example 30-40% w/w of the composition, for example 30-35% w/w of the composition. For example the medium-chain triglyceride may make up 40-70% w/w of the composition, for example 50-70% w/w of the composition, for example, 55-65% w/w of the composition The weight ratio of the medium-chain triglyceride component to the urolithin is generally in the range 0.01:1 to 100:1, for example 0.5:1 to 100:1, for example 0.5:1 to 50:1, for example 0.5:1 to 5:1; or, for example, 1:1 to 75:1, for example 1:1 to 50:1, for example 1:1 to 20:1, for example 1:1 to 10:1, for example 1:1 to 2.5:1, for example 1:1 to 2:1, for example 1:1 to 1.5:1. The weight ratio of the medium-chain triglyceride component to the urolithin may be in the ratio 0.01:1 to 10:1, for example 0.1:1 to 10:1 or 0.01:1 to 5:1, for example 0.01:1 to 0.1:1. The composition of the invention generally has the consistency of a viscous liquid or paste, and it can be provided as a single serving supplement to a subject's general diet (for example in a bar, gel or a softgel capsule, hard capsule, or diluted in a drink); alternatively, it can be provided as a part or the whole of every meal.

The urolithin typically makes up from 0.1 to 80% w/w of the composition of the invention, for example 0.1 to 60% w/w, for example 0.25 to 50% w/w. For example the urolithin may make up 0.5-50% w/w of the composition. If the composition is provided as a part or the whole of a meal then the urolithin may make up for example 0.25-5% w/w of the composition, for example, 0.3-3% w/w of the composition. If the composition of the invention is provided as a single serving supplement to a subject's general diet, then the urolithin typically makes up from 20 to 80% w/w of the composition, for example 20 to 40% w/w, for example 25 to 35% w/w of the composition of the invention. For example the urolithin may make up 26-34% w/w of the composition, for example, 28-33% w/w of the composition; for example, 29-32% w/w of the composition, for example 29-31% w/w of the composition.

Medium-Chain Triglycerides:

Medium-chain triglycerides are compounds of formula $CH_2(OR^1)$—$CH(OR^2)$—$CH_2(OR^3)$ where $R^1$, $R^2$ and $R^3$ are medium chain fatty acid groups, generally of formula —$C(=O)(CH_2)_n CH_3$ where n is in the range 4 to 10, for example 6 to 8. Medium-chain fatty acids are fatty acids which have an aliphatic tail of 6-12 carbon atoms. The aliphatic tail is predominantly saturated. Particular medium-chain fatty acids include caproic acid (hexanoic acid, C6:0), caprylic acid (octanoic acid, C8:0), capric acid (decanoic acid, C10:0) and lauric acid (dodecanoic acid, C12:0). Myristic acid (tetradecanoic acid, C14:0) can also be present in minor amounts. Medium-chain triglycerides most commonly used generally have a mixture of triglycerides of caprylic acid and capric acid, and contain 95% or greater of saturated fatty acids. The medium chain triglyceride component in the composition of the invention can consist of a homogeneous, single medium chain triglyceride compound type; more commonly, the medium chain triglyceride component in the composition of the invention is a mixture of two or more different medium chain triglyeride compounds.

The European Pharmacopoeia describes medium-chain triglycerides as the fixed oil extracted from the hard, dried fraction of the endosperm of *Cocos nucifera* L. (coconut) or from the dried endosperm of *Elaeis guineenis* Jacq. (African oil palm). The European Pharmacopoeia and the USPNF both have specifications for medium-chain triglycerides that require the presence of particular fatty acids is as follows: caproic acid (C6) ≤2.0%; caprylic acid(C8) 50.0-84.0%; capric acid (C10) 20.0-50.0%; lauric acid (C12) ≤3.0%; and myristic acid (C14) ≤1%.

In particular, medium-chain triglycerides for use in compositions of the invention comprise a mixture of triglycerides with fatty acid chains present in the following proportions: C6 ≤5%; C8 50-70%; C10 30-50%; and C12 ≤12%, for example C6 ≤0.5%; C8 55-65%; C10 35-45%; and C12 ≤1.5%.

Medium-chain triglycerides for use in compositions of the invention may be derived from any known or otherwise suitable source. Medium-chain triglycerides can be extracted from natural sources, or synthesised from glycerol and suitable fatty acids under appropriate conditions. Non-limiting examples of commercial sources for extraction of medium-chain triglycerides (or for medium-chain fatty acids that can be used in the synthesis of medium chain triglycerides), include coconut oil and palm oil, as well as dairy fat, in particular butter. Combinations of sources or types of medium-chain triglycerides may be used.

Medium-chain triglycerides for use in compositions of the invention may be obtained commercially as liquid or solid preparations, and as simple or complex combinations with sugars, vitamins, essential fatty acids and minerals. Medium-chain triglycerides are also available in the form of oil or margarine.

Urolithins:

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structure (I) shown above. The structures of some particularly common urolithins are described in Table 1 below, with reference to structure (I).

|  | Substituent of structure (I) | | | | | |
|---|---|---|---|---|---|---|
|  | A | B | C | D | W, X and Y | Z |
| Urolithin A | H | H | H | OH | H | OH |
| Urolithin B | H | H | H | H | H | OH |
| Urolithin C | H | H | OH | OH | H | OH |
| Urolithin D | OH | H | OH | OH | H | OH |
| Urolithin E | OH | OH | H | OH | H | OH |
| Isourolithin A | H | H | OH | H | H | OH |
| Isourolithin B | H | H | OH | H | H | H |
| Urolithin M-5 | OH | OH | OH | OH | H | OH |
| Urolithin M-6 | H | OH | OH | OH | H | OH |
| Urolithin M-7 | H | OH | H | OH | H | OH |

In practice, for commercial scale products, it is convenient to synthesise the urolithins. Routes of synthesis are described, for example, in WO2014/004902.

Urolithins of any structure according to structure (I) may be used in compositions of the invention. Particularly suitable compounds for use in compositions of the invention are the naturally-occurring urolithins. Thus, Z is preferably OH and W, X and Y are preferably all H. When W, X and Y are all H, and A, and B are both H, and C, D and Z are all OH, then the compound is Urolithin C. When W, X and Y are all H, and A, B and C are all H, and D and Z are both OH, then the compound is Urolithin A. Preferably, the Urolithin used in a formulation of the invention is Urolithin A, Urolithin B, Urolithin C or Urolithin D. Most preferably, the Urolithin used in a formulation of the invention is Urolithin A.

Urolithin A

Preferably, urolithin for use in compositions of the invention is micronized. Micronization enables the urolithin to disperse or dissolve more rapidly. If micronized urolithin is used, then preferably, the urolithin has a $D_{50}$ size of under 100 μm—that is to say that 50% of the urolithin by mass has a particle diameter size of under 100 μm. More preferably, the urolithin has a $D_{50}$ size of under 75 μm, for example under 50 μm, for example under 25 μm, for example under 20 μm, for example under 10 μm. More preferably, the urolithin has a $D_{50}$ in the range 0.5-50 μm, for example 0.5 to 20 μm, for example 0.5 to 10 μm, for example 1.0 to 10 μm, for example 1.5 to 7.5 μm, for example 2.8 to 5.5 μm. Preferably, the urolithin has a $D_{90}$ size of under 100 μm. More preferably, the urolithin has a $D_{90}$ size of under 75 μm, for example under 50 μm, for example under 25 μm, for example under 20 μm, for example under 15 μm. The urolithin preferably has a $D_{90}$ in the range 5 to 100 μm, for example 5 to 50 μm, for example 5 to 20 μm, for example 7.5 to 15 μm, for example 8.2 to 16.0 μm. Preferably, the urolithin has a $D_{10}$ in the range 0.5-1.0 μm. Preferably, the urolithin has a $D_{90}$ in the range 8.2 to 16.0 μm, a $D_{50}$ in the range 2.8 to 5.5 μm and a $D_{10}$ in the range 0.5 to 1.0 μm. Micronisation can be achieved by methods established in the art, for example compressive force milling, hamermilling, universal or pin milling, or jet milling (for example spiral jet milling or fluidised-bed jet milling) may be used. Jet milling is especially suitable.

Phosphatidylcholine

Compositions of the invention may, advantageously, comprise one or more phospholipids. A particularly preferred phospholipid for use in compositions of the invention is phosphatidylcholine. The advantages brought about by phosphatidylcholine may be due, at least in part, to their amphipathic nature.

A particularly useful source of phospholipids, in particular phosphatidylcholine, for use in the invention is lecithin, and compositions of the invention advantageously comprise lecithin. Lecithin, when present in compositions of the invention, typically makes up at least 0.5% w/w of the composition of the invention, preferably at least 1% w/w of the composition of the invention. The lecithin preferably makes up 10% w/w or more of the composition, for example 20% w/w or more by weight, for example 30% w/w or more by weight of the composition. For example the lecithin may make up 0.5-80% w/w of the composition, for example 1-80% w/w, for example 20-80% w/w, for example 40-80% w/w, alternatively for example 0.5-75% w/w of the composition, for example, 1-40% w/w of the composition, for example 30-40% w/w of the composition, for example 30-35% w/w of the composition, for example, 30-75% w/w of the composition. Alternatively, the lecithin may make up 0.5-5% w/w of the composition, for example 1-5% w/w of the composition, for example 1-3% w/w of the composition, for example, 0.5-2% w/w of the composition, for example, 1-2% w/w of the composition. The weight ratio between the lecithin, when present, and the urolithin is generally in the range 0.02:1 to 3:1, for example, 0.03:1 to 1.2:1, for example 1:1 to 1.2:1, for example 1.1:1 to 1.2:1.

'Lecithin' designates any group of fatty substances occurring in animal and plant tissues including phosphoric acid, choline, fatty acids, glycerol, glycolipids, triglycerides, and phospholipids (e.g., phosphatidylcholine, phosphatidylethanolamine, and phosphatidylinositol). In particular, commercial lecithin obtained from soya and sunflower comprises the phospholipids phosphatidyl choline, phosphatidyl inositol, phosphatidyl ethanolamine, and phosphatidic acid. Lecithin may be obtained by chemical extraction from its source in a non-polar solvent such as hexane, ethanol, acetone, petroleum ether or benzene, or by mechanical extraction. In particular, lecithin may be obtained by extraction from sources including soybeans, eggs, milk, rapeseed, cottonseed and sunflower. Commercial lecithin for use in edible formulations may be readily purchased.

Commercially produced lecithin, which may be used in formulations of the invention, typically contains the following major components: 33-35% soybean oil, 20-21% inositol phosphatides, 19-21% phosphatidylcholine, 8-20% phosphatidylethanolamine, 5-11% other phosphatides, 5% free carbohydrates, 2-5% sterols and 1% moisture.

Commercially produced lecithin, which may be used in formulations of the invention, may be enriched with phosphatidylcholine, having a minimum of 5% w/w phosphatidylcholine in the lecithin, for example, having a minimum of 10% w/w phosphatidylcholine in the lecithin, for example, having a minimum of 15% w/w phosphatidylcholine in the lecithin, for example, having a minimum of 20% w/w phosphatidylcholine in the lecithin, for example, having a minimum of 25% w/w phosphatidylcholine in the lecithin, for example, having a minimum of 30% w/w phosphatidylcholine in the lecithin, for example, having a minimum of 32% w/w phosphatidylcholine in the lecithin, for example, having a minimum of 40% w/w phosphatidylcholine in the lecithin.

Lecithins may also be modified by one or more of the following processes to tailor their properties: alcohol extraction of particular phospholipids to produce a lecithin with a modified ratio of differing phospholipids; acetone extraction to remove oil, resulting in a powdered or granulated phospholipid blend; spray drying onto proteins as carriers; spray cooling with synthetic emulsifiers such as high melting mono- and di-glycerides to produce flaked or powdered products; modification by enzyme action (phospholipases, commonly in particular phospholipase A2), in particular partial hydrolysis to produce lecithins with pronounced emulsifying behaviour; hydrolysis of fatty acid groups by acids and alkali; acetylation, and hydroxylation of fatty acid chains and amino groups.

Forms of Compositions:

The compositions of the invention can take any suitable physical form. They may be in the form of a solid (for example a bar), a semi-solid (for example a softgel, capsule (for example a hard capsule) or dragee), or a liquid (including emulsions). In many instances, the compositions of the invention are in the form of a viscous fluid or a paste. By selecting suitable medium chain triglycerides and excipients, the physical form of the composition can be tailored to the requirements of the product in question. The compositions of the invention may be pharmaceutical compositions. The compositions of the invention may be nutritional compositions.

A softgel composition may be provided in a capsule having a shell. The shell may be of a conventional type, for example it may be a soft gelatin-based shell. The compositions of this invention may also be inside of a hard capsule type of shell.

A bar may be of any suitable type and it may contain ingredients conventionally used for the preparation of snack bars.

Semi-solid forms may likewise contain excipients conventional in the art. The excipients can, for example, provide a desired hardness, shelf-life and flavour such that the composition has an acceptable taste, an attractive appearance and good storage stability. Semi-solid forms can be in the form of a paste.

Liquid compositions may be in the form of a medicine, a dietary supplement, or a beverage, each for oral consumption. Liquid formulations may be solutions, emulsions, slurries or other semi-liquids. Excipients in a liquid composition can, for example, provide a shelf-life, visual appearance, flavour and mouthfeel such that the composition has an acceptable taste, an attractive appearance and good storage stability. At certain levels of dilution, a drink may need to be shaken before the subject drinks it, so as to maintain an even suspension of the active ingredient.

Additional Components in Compositions of the Invention:

The composition according to the invention may contain additional components beyond the urolithin and the medium-chain triglyceride. The additional components may be compounds that provide health benefits, for example selected from vitamins, minerals, polyunsaturated fatty acids, and other compounds.

Amongst vitamins, there may specifically be mentioned Vitamin A, Vitamin C, Vitamin D, Vitamin E, Vitamin B12 and Vitamin K2. As used herein, "vitamin D" refers, to any of known form of vitamin D, and specifically includes vitamin D2 (ergocalciferol), vitamin D3 (cholecalciferol), vitamin D precursors, metabolites and another analogues, and combinations thereof, as well as the various active and inactive forms of vitamin D. For example, vitamin D3 may be provided in its unhydroxylated inactive form as cholecalciferol, or may be provided in its hydroxylated active form as calcitriol.

Creatine has been described as having beneficial effects in the treatment of muscle disorders. It can be included in composition of the invention. β-hydroxyl-β-methylbutyrate (HMB) has been described as having beneficial effects in the treatment of muscle disorders. It can be included in composition of the invention.

Polyunsaturated fatty acids are fatty acids that contain more than one double bond in the backbone. This class includes many important compounds, such as essential fatty acids, e.g., omega-3 and omega-6 fatty acids. Long chain polyunsaturated fatty acids are suitable, and preferably those having at least 20 carbon atoms in the molecule. Such long chain omega-3 fatty acids include cis-11, 14, 17-eicosatrienoic acid (ETE) C20:3, cis-8, 11, 14, 17-eicosatetraenoic acid (ETA) C20:4, cis-5,8,11, 14, 17-eicosapentaenoic acid (EPA) C20:5, cis-7, 10, 13, 16, 19-docosapentaenoic acid (DPA, Clupanodonic acid) C22:5, cis-4, 7, 10, 13, 16, 19-docosahexaenoic acid (DHA) C22:6, cis-9, 12, 15, 18,21-tetracosapentaenoic acid C24:5; cis-6,9, 12, 15, 18,21-tetracosahexaenoic acid (Nisinic acid) C24:6. Long chain omega-6 fatty acids having at least 20 carbon atoms include cis-11, 14-eicosadienoic acid C20:2, cis-8, 11, 14-eicosatrienoic acid (Dihomo-gamma-linolenic acid) (DGLA) C20:3, cis-5,8, 11, 14-eicosatetraenoic acid (Arachidonic acid) (AA) C20:4, cis-13, 16-docosadienoic acid C22:2, cis-7, 10, 13, 16-docosatetraenoic acid (Adrenic acid) C22:4, cis-4, 7, 10, 13, 16-docosapentaenoic acid (Osbond acid) C22:5. The composition according to the invention preferably contains EPA, DHA or a combination of them, for example in an amount from 10 to 1,000 mg per serving; for example in an amount from 25 to 250 mg per serving.

Pharmaceutical compositions of the invention may include additional pharmaceutically active compounds.

In some exemplary embodiments, the compositions of the present invention may comprise, in addition to medium-chain triglycerides and urolithin, one or more additional macronutrients, typically fat or carbohydrate, or fat and carbohydrate.

Non-limiting examples of suitable fats or sources thereof for use in the compositions described herein include coconut oil; fractionated coconut oil; soy oil; corn oil; olive oil; safflower oil; high oleic safflower oil; sunflower oil; high oleic sunflower oil; palm and palm kernel oils; palm olein; canola oil; marine oils; cottonseed oils; polyunsaturated fatty acids such as docosahexaenoic acid (DHA), arachidonic acid (ARA), eicosapentaenoic acid (EPA); and combinations thereof.

Non-limiting examples of suitable carbohydrates or sources thereof for use in the compositions described herein may include maltodextrin, hydrolyzed or modified starch or cornstarch, glucose polymers, corn syrup, corn syrup solids, rice-derived carbohydrates, glucose, fructose, lactose, high fructose corn syrup, tapioca dextrin, isomaltulose, sucromalt, maltitol powder, glycerin, fructooligosaccharides, soy fiber, corn fiber, guar gum, konjac flour, polydextrose, honey, sugar alcohols (e.g., maltitol, erythritol, sorbitol), and combinations thereof. Maltodextrin, sucrose and fructose are especially preferred.

The total concentrations or amounts of the fat and carbohydrates and other components vary depending upon the nutritional needs of the intended user.

Additional components in a composition of the invention may be compounds that do not provide health benefits to the subject, but instead improve the composition in some other way, for example its taste, texture or shelflife as mentioned above. The composition of the invention may thus further contain one or more compounds selected from emulsifiers, colorants, preservatives, gums, setting agents, thickeners, sweeteners and flavourings.

Suitable emulsifiers, stabilisers, colorants, preservatives, gums, setting agents and thickeners are well known in the art of manufacture of emulsions and other semi-liquids. Emulsifiers may include one or more of phosphatidylcholine, lecithin, polysorbates such as polysorbate 60 or polysorbate 80 (Tween-60 and Tween-80), and glycerol monostearate (GMS). Glycerol monostearate is also known as glyceryl monostearate. Metal chelators or sequestrants such as sodium calcium salts of ethylenediamine tetra acetic acid (EDTA) may also be used. Other components that may be included in formulations of the invention include polyethylene glycols, silicon dioxide, vegetable shortening and beeswax.

Stabilisers may be used in a composition of the invention. Many compositions of the invention are stable suspensions without the need for an added stabiliser. A stable suspension is one that does not undergo a phase separation over time. For certain compositions of the invention, the stability can be improved by inclusion of an added stabiliser. Suitable stabilisers for use in compositions of the invention include glycerol monostearate (GMS), silicon dioxide and vegetable shortening. An exemplary stabiliser is GMS and preferred compositions of the invention contain GMS. Its properties also make GMS a good solvent for phospholipids, such as found in lecithin for example. GMS exists in two polymorphs: the α-form is dispersible and foamy, useful as an emulsifying agent or preservative. The β-form is suitable for wax matrices. The α-form is converted to the β-form when heated at 50° C.

GMS falls into two distinct grades: 40-55 percent monoglycerides, and 90 percent monoglycerides. 40-55 percent monoglycerides as defined by the European Pharmacopoeia describes GMS as a mixture of monoacylglyceros, mostly monostearoylglycerol, together with a quantity of di- and tri-glycerols. In particular, the 40-55 grade contains 40-55% monoacylglycerols, 30-45% diacylglycerols, and 5-15% of triacylglycerols. The 99 percent grade contains not less than 90% of monoglycerides. The monoglycerides in commercial GMS products are mixtures of variable proportions of glyceryl monostearate and glyceryl monopalmitate. The European Pharmacopoeia further divides glyceryl monostearate 40-55 into three types according to the proportion of stearic ester in the mixture. Type 1 contains 40.0-60.0% stearic acid, and the sum of palmitic and stearic acids is ≤90%. Type 2 contains 60.0-80.0% stearic acid, and the sum of palmitic and stearic acids is ≤90%. Type 3 contains 90.0-99.0% stearic acid, and the sum of palmitic and stearic acids is ≤96%. Any form of GMS may be used in compositions of the invention.

A flavouring may be especially beneficial in a composition of the invention. In a liquid or semi-liquid composition, fruit flavour can be provided by inclusion of a fruit sauce or puree. Typical flavorings include strawberry, raspberry, blueberry, apricot, pomegranate, peach, pineapple, lemon, orange and apple. Generally, fruit flavorings include fruit extract, fruit preserve or fruit puree, with any of a combination of sweeteners, starch, stabilizer, natural and/or artificial flavors, colorings, preservatives, water and citric acid or other suitable acid to control the pH.

Dosing

The effective amount of the composition to be taken will vary depending upon the manner of administration, the age, body weight, and general health of the subject. Factors such as the disease state, age, and weight of the subject may be important, and dosage regimens may be adjusted to provide the optimum response.

Daily intake of the urolithin (for example Urolithin A) component is typically in the range of 10 mg to 5 g per day, for example 20 mg to 2500 mg per day, for example 50 mg to 1500 mg per day, for example 100 mg to 1,500 mg per day, for example 150 mg to 1,500 mg per day, for example 200 mg to 1,500 mg per day, for example 250 mg to 1500 mg per day, for example 50 mg to 1000 mg per day, for example 250 mg to 1000 mg per day. In one embodiment, the composition is taken in an amount to provide a dosage of urolithin in the range from about 0.2 mg/kg/day to greater than about 100 mg/kg/day. For example, the dosage of urolithin may be 0.2 to 100, 0.2 to 50, 0.2 to 40, 0.2 to 25, 0.2 to 10, 0.2 to 7.5, 0.2 to 5, 0.25 to 100, 0.25 to 25, 0.25 to 25, 0.25 to 10, 0.25 to 7.5, 0.25 to 5, 0.5 to 50, 0.5 to 40, 0.5 to 30, 0.5 to 25, 0.5 to 20, 0.5 to 15, 0.5 to 10, 0.5 to 7.5, 0.5 to 5, 0.75 to 50, 0.75 to 25, 0.75 to 20, 0.75 to 15, 0.75 to 10, 0.75 to 7.5, 0.75 to 5, 1.0 to 50, 1 to 40, 1 to 25, 1 to 20, 1 to 15, 1 to 10, 1 to 7.5, 1 to 5, 2 to 50, 2 to 25, 2 to 20, 2 to 15, 2 to 10, 2 to 7.5, or 2 to 5 mg/kg/day.

A unit dose composition of the invention preferably contains 10 mg to 5 g of urolithin, for example 20 mg to 2500 mg, for example 50 mg to 1500 mg, for example 250 mg to 1500 mg, for example 50 mg to 1000 mg, for example 100 mg to 1000 mg, for example 250 mg to 1000 mg. A unit dose may be in the form of a snack bar; a snack bar of weight 25 to 150 g (for example 40 to 100 g) may contain the necessary amount of urolithin. A unit dose composition may alternatively be in the form of a drink, for example provided in a container (for example a pouch) of a volume suitable for a single dose (for example 100 to 300 ml). A drink of 25 ml to 500 ml (for example 50 ml to 300 ml) may contain the necessary amount of urolithin. A drink providing the composition of the invention may contain the urolithin at a concentration of 0.1 to 50 mg per ml, 0.25 to 25 mg per ml, for example 0.5 to 10 mg per ml, for example 1 to 5 mg per ml. A unit dose may alternatively be in the form of one or more semi-solid doses, such as a softgel or a paste. A single softgel capsule may contain a urolithin dose of, for example, 25 mg, 50 mg, 75 mg, 100 mg, 150 mg, 200 mg, 250 mg, 300 mg, 350 mg, 400 mg, 450 mg or 500 mg, for example 250 mg.

Ratio ranges of the components of the compositions of the invention are described above. A composition of the invention may contain 10 mg to 15 g of medium-chain triglyceride and 10 to 5000 mg of urolithin; for example 20 to 7500 mg of medium-chain triglyceride and 20 to 2500 mg of urolithin; for example 25 mg to 2,500 mg of medium-chain triglyceride and 50 to 1500 mg of urolithin; for example 50 mg to 4500 mg of medium-chain triglyceride and 50 to 1500 mg of urolithin; for example 250 to 4500 mg of medium-chain triglyceride and 250 to 1500 mg of urolithin; for example 50 to 3000 mg of medium-chain triglyceride and 50 to 1000 mg of urolithin; for example 250 to 3000 mg of medium-chain triglyceride and 250 to 1000 mg of urolithin. The compositions preferably further contain lecithin. The compositions also further preferably contain an additional stabiliser, for example glycerol monostearate.

A representative composition is shown in Table 1:

TABLE 1

Representative formulation A:

| Composition | Per 100 g |
|---|---|
| Medium Chain Triglycerides | 10-85 g |
| Urolithin A | 10-50 g |
| Lecithin (comprising minimum phosphatidylcholine content of 32% w/w) | 10-50 g |
| Glycerol Monostearate | 0-5 g |

Compositions of the invention contain urolithin and medium-chain triglycerides. The composition of the invention may contain, for example, 20-85% w/w medium-chain triglycerides and 15-70% w/w urolithin, for example 40-80% w/w medium-chain triglycerides and 20-60% w/w urolithin, for example 50-70% w/w medium-chain triglycerides and 30-50% w/w urolithin, for example 60-75% w/w medium-chain triglycerides and 25-40% w/w urolithin.

Preferred compositions of the invention comprise urolithin, medium-chain triglycerides and an emulsifier such as phosphatidylcholine, for example a lecithin. For example, the composition of the invention may contain 10-80% w/w medium-chain triglycerides, 5-70% w/w urolithin and 0.5-65% w/w lecithin; the composition of the invention may contain 20-70% w/w medium-chain triglycerides, 15-70% w/w urolithin and 0.5-50% w/w lecithin; for example 25-50% w/w medium-chain triglycerides, 20-50% w/w urolithin and 20-50% w/w lecithin; for example 30-40% w/w medium-chain triglycerides, 25-35% w/w urolithin, and 30-40% w/w lecithin. Alternatively, compositions of the invention comprising urolithin, medium chain triglycerides and lecithin may contain, for example, 60-75% w/w medium-chain triglycerides, 25-40% w/w urolithin and 0.5-5% w/w lecithin.

Further preferred compositions of the invention may comprise urolithin, medium-chain triglycerides, an emulsifier such as lecithin, and a stabiliser such as GMS. For example, the composition of the invention may contain 25-75% w/w medium-chain triglycerides, 20-50% w/w urolithin, 0.5-50% w/w lecithin and 0.5-5% w/w GMS; for example 30-40% w/w medium-chain triglycerides, 25-35% w/w urolithin, 30-40% w/w lecithin and 0.5-3% w/w GMS. Alternatively, compositions of the invention comprising urolithin, medium chain triglycerides, lecithin and GMS may contain, for example, 60-75% w/w medium-chain triglycerides, 25-40% w/w urolithin, 0.5-5% w/w lecithin and 0.5-3% w/w GMS.

Further compositions of the invention may comprise urolithin, medium-chain triglycerides, an emulsifier such as lecithin and/or Tween (polysorbate), and a stabiliser such as GMS. For example, the composition of the invention may contain 25-75% w/w medium-chain triglycerides, 20-50% w/w urolithin, 0.5-50% w/w lecithin, 0.5-5% w/w GMS and 1-10% w/w Tween-60, for example, 60-75% w/w medium-chain triglycerides, 25-40% w/w urolithin, 0.5-5% w/w lecithin, 0.5-3% w/w GMS and 1-5% w/w Tween-60.

Treatments:

The composition of the invention can be taken as a single treatment or, more commonly, as a series of treatments. In one example, a subject takes a dose before or after exercise. For a subject who is not able to exercise, a dose of the composition may, for example, be taken once, twice or three times per day, or one, two, three, four, five or six times per week. In another example, the intervention may be taken by a subject independent of the subject's ability or need to exercise. It will also be appreciated that the effective dosage of the compound may increase or decrease over the course of a particular treatment.

Medical and Non-Medical Treatments:

The composition of the invention can be for use as a medicament. The composition can be used as a dietary supplement, as a functional food and as a medical food. The composition of the invention is thus useful in the treatment of various diseases as well as health conditions not considered to be a disease. In particular, disease and non-disease health conditions may be characterised by an inadequate mitochondrial activity. The composition finds use in the treatment of both diseases and disease states. The composition finds use in the management normal physiological function in healthy individuals of conditions characterised by poor physical performance, impaired endurance capacity, and impaired muscle function. Compositions of the invention may improve physical performance in individuals with a disease, including young and elderly individuals. Compositions of the invention may improve physical performance, for example, short-term performance or long-term performance in healthy individuals, including athletes, non-athletic individuals, sedentary individuals and the elderly. This improvement of performance may be measured by the time spent to walk or run a certain distance (for example, an improved performance during the 6 minute walk test (MWT)), an improved time to run a certain distance, an improved IPAQ score on the international physical activity questionnaire, an increased number of chair-stands in a certain time, or another test designed to measure physical performance.

Compositions of the invention further provide for the improvement of endurance capacity. The endurance capacity refers to the time to fatigue when exercising at a constant workload, generally at an intensity <80% $VO_{2max}$. Compositions of the invention may improve endurance capacity in individuals with a disease, including young and elderly individuals. Compositions of the invention may improve endurance capacity in healthy individuals, including athletes, non-athletic individuals, sedentary individuals and the elderly. The invention provides for a method of increasing the time to fatigue while performing a specific activity, for example, fitness training, walking, running, swimming, or cycling. This improvement of endurance capacity may be assessed with objective measurements (for example, speed, oxygen consumption or heart rate) or it can be self-reported measurements (for example, using a validated questionnaire).

The invention further provides a composition to improve, maintain or reduce the loss of muscle function. Compositions of the invention may improve, maintain or reduce the loss of muscle function in individuals with a disease, including young and elderly individuals. Compositions of the invention may improve, maintain or reduce the loss of muscle function in healthy individuals, including athletes, non-athletic individuals, sedentary individuals and the elderly. For example, compositions of the invention may increase muscle strength as evidenced by the improvement of performing a physical activity, such as an exercise, for example, increased ability to lift weights or increased hand grip strength. Also, compositions of the invention may improve muscle structure, for example by increasing or maintaining muscle mass in conditions of normal muscle function, declining muscle function or impaired muscle function.

This invention further provides a composition to improve the physical performance or endurance capacity as perceived by the individual. For example, by the reduction of in perceived exertion or effort during exercise or an activity as determined using a self-reported questionnaire.

The invention further provides a composition of the invention for use in the treatment of a variety of conditions including conditions related to inadequate mitochondrial activity, including obesity, reduced metabolic rate, metabolic syndrome, diabetes mellitus, cardiovascular disease, hyperlipidemia, memory decline, neurodegenerative diseases, cognitive disorder, mood disorder, stress, and anxiety disorder, fatty liver disease (for example NAFLD and NASH), for improving liver function and for weight management. In particular, the compositions of the invention find use in the treatment of muscle-related pathological conditions. Accordingly, the invention provides a composition of the invention for use in the treatment of a muscle-related pathological condition. The invention also provides a method of treating a muscle-related pathological condition in a subject comprising administering to the subject an effective amount of a composition of the invention. Muscle-related conditions include both conditions impacting generally healthy individuals as well as pathological conditions. Such muscle conditions found in healthy people or people affected by a disease include musculoskeletal diseases or disorders; cachexia; muscle wasting; age related decline in muscle function; pre-frailty; frailty; myopathies; neuromuscular diseases, such as Duchenne muscular dystrophy and other dystrophies; age-related sarcopenia; acute sarcopenia; muscle atrophy and/or cachexia, for example muscle atrophy and/or cachexia associated with burns, bed rest, limb immobilization, or major surgery, including thoracic, abdominal, and/or orthopedic surgery; and muscle degenerative disease.

Examples of age-related conditions that may be treated with compositions of the invention include sarcopenia and muscle wasting.

The myopathy may also be caused by a muscular dystrophy syndrome, such as Duchenne, It has been reported in WO2014/111580 that Urolithin B (but not Urolithin A) increased the mean diameter of myotubes in vitro. The effect was not seen with Urolithin A.

Non-Medical Treatments:

The composition of the invention is useful in enhancing muscle performance. The invention thus provides a composition of the invention for use in enhancing muscle performance. The invention also provides a method of enhancing muscle performance by administering to a subject an effective amount of a composition of the invention. Administration can be self-administration. The enhanced muscle performance may be one or more improved muscle function, improved muscle strength, improved muscle endurance and improved muscle recovery.

The composition of the invention can thus be used in a method of improving physical endurance (e.g., ability to perform a physical task such as exercise, physical labor, sports activities), inhibiting or retarding physical fatigue, enhancing working capacity and endurance, reducing muscle fatigue, enhancing cardiac and cardiovascular function.

Improved muscle function can be particularly beneficial in elderly subjects with reduced muscle function as a result of an age-related condition. For example, a subject who may benefit from improved muscle function may experience a decline in muscle function which then leads to pre-frailty and frailty. Such subjects may not necessarily experience muscle wastage in addition to their decline in muscle function. Some subjects do experience both muscle wasting and a decline in muscle function, for example subjects with sarcopenia. The composition of the invention may be used in enhancing muscle performance by administering a composition of the invention to a subject who is frail or pre-frail.

Muscle performance may be sports performance, which is to say the ability of an athlete's muscles to perform when participating in sports activities. Enhanced sports performance, strength, speed, and endurance are measured by an increase in muscular contraction strength, increase in amplitude of muscle contraction, or shortening of muscle reaction time between stimulation and contraction. Athlete refers to an individual who participates in sports at any level and who seeks to achieve an improved level of strength, speed, or endurance in their performance, such as, for example, body builders, bicyclists, long distance runners, and short distance runners. Enhanced sports performance is manifested by the ability to overcome muscle fatigue, ability to maintain activity for longer periods of time, and have a more effective workout.

EXAMPLES

The following Examples illustrate the invention.

Compounds

Urolithin A was prepared as follows:

Urolithin A (4) was prepared in two steps starting from 2-bromo-5-methoxybenzoic acid 1 and resorcinol 2. The pure compound was obtained as a pale yellow powder.

Step 1:

A mixture of 2-bromo-5-methoxybenzoic acid 1 (27.6 g; 119 mmol; 1.0 eq.), resorcinol 2 (26.3 g; 239 mmol; 2.0 eq.) and sodium hydroxide (10.5 g; 263 mmol; 2.2 eq.) in water (120 mL) was heated under reflux for 1 hour. A 5% aqueous solution of copper sulphate (3.88 g of $CuSO_4 \cdot 5H_2O$ in 50 mL water; 15.5 mmol; 0.1 eq.) was then added and the mixture was refluxed for additional 30 minutes. The mixture was allowed to cool to room temperature and the solid was filtered on a Buchner filter. The residue was washed with cold water to give a pale red solid which was triturated in hot MeOH. The suspension was left overnight at 4° C. The resultant precipitate was filtered and washed with cold MeOH to yield the title compound 3 as a pale brown solid.

Step 2:

To a suspension of 3 (10.0 g; 41 mmol; 1.0 eq.) in dry dichloromethane (100 mL) was added dropwise at 0° C. a 1 M solution of boron tribromide in dry dichloromethane (11.93 mL of pure $BBr_3$ in 110 mL of anhydrous dichloromethane; 124 mmol; 3.0 eq.). The mixture was left at 0° C. for 1 hour and was then allowed to warm up to room temperature. The solution was stirred at that temperature for 17 hours. Then ice was added thoroughly to the mixture. The yellow precipitate was filtered and washed with cold water to give a yellow solid which was heated to reflux in acetic acid for 3 hours. The hot solution was filtered quickly and the precipitate was washed with acetic acid, then with diethyl ether to yield the title compound 4 as a yellow solid. $^1H$ and $^{13}C$ NMR were in accordance with the structure of 4.

Example 1: Bioavailability Study of Urolithin a Formulated with or without Medium-Chain Triglycerides Male Sprague-Dawley rats were administered by oral gavage after overnight fasting with either a saline suspension of urolithin A with no further excipients, or with further formulations of Urolithin A with various excipients, at a dose corresponding to 60 mg/kg/day. The urolithin used in the formulations was micronized with a particle size distribution of $D_{90}$=91 μm to 15 μm and $D_{50}$=2 μm to 9 μm. The actual particle size was $D_{90}$=11.5, $D_{50}$=3.9 and a $D_{10}$=0.7 μm. The components by % w/w of the formulations used are shown in Table 2 below.

TABLE 2

Formulations used in bioavailability study.

| Component | Formulation 65 | Formulation 66 | Formulation 67 | Formulation 68 |
|---|---|---|---|---|
| Urolithin A | 30.1 | 30.1 | 26.3 | 26.3 |
| Medium-chain triglycerides | 64.3 | 34.2 | | |
| Lecithin | 1.1 | 34.2 | 72.9 | 70.3 |
| Glycerol Monostearate | 1.4 | 1.4 | 0.8 | 0.8 |
| Tween-60 | 3.0 | | | 2.6 |

The medium-chain triglycerides were obtained from Cremer Oleo GmbH & Co KG, under the product name CremerCOOR MCT 60/40 EP, which contains C6 ≤0.5%; C8 55-65%; C10 35-45%; and C12 ≤1.5%.

The lecithin was obtained from Cargill, Inc., under the product name Epikuron® 135 F IP, which contains minimum 32% phosphatidylcholine.

The glycerol monostearate was obtained from Cremer Oleo GmbH & Co KG, under the product name IMWITOR® 900 (F) P, which contains 40.0-50.0% monoacylglycerols, 30.0-45.0& diacylglycerols, and 5.0-15.0% triacylglycerols.

Figure 1:
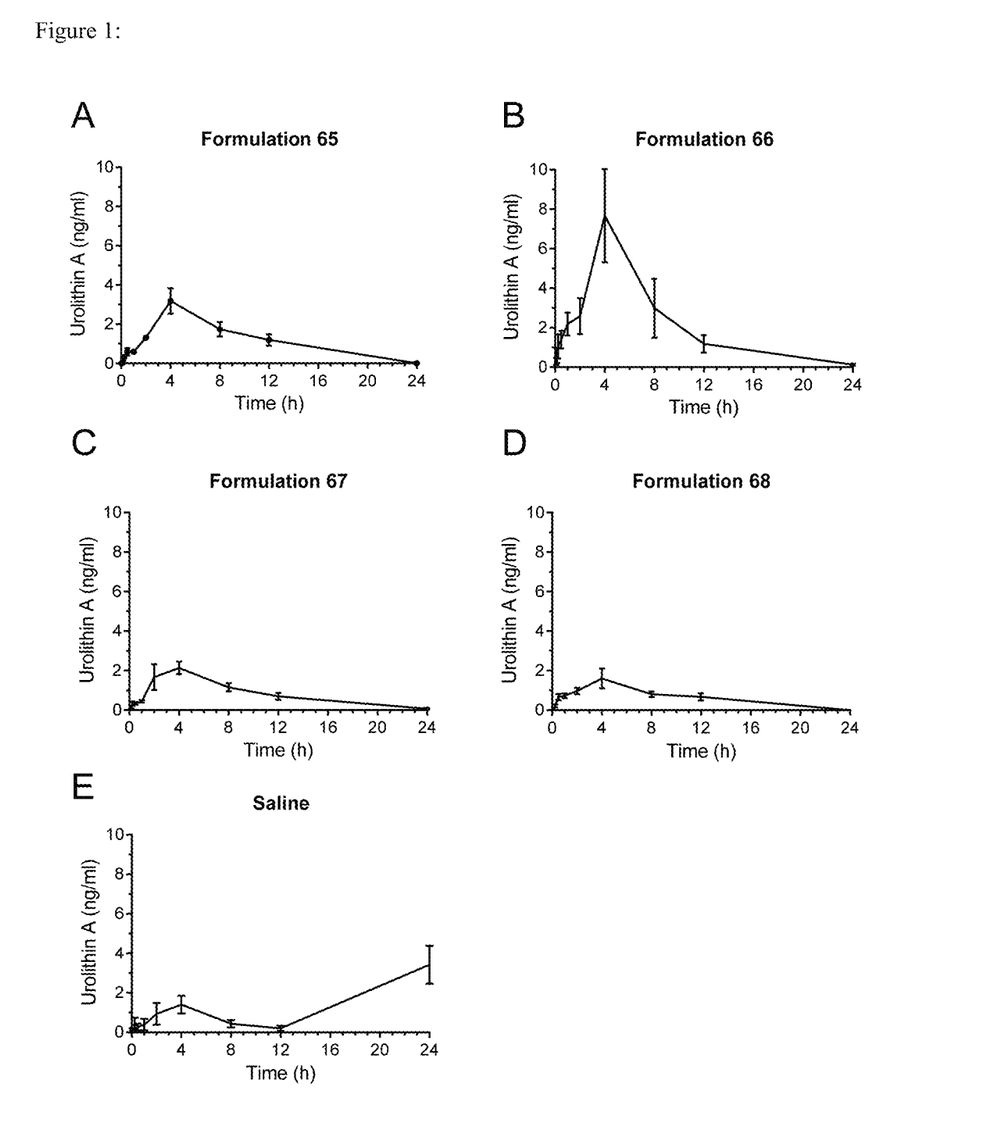
FIG. 1 shows the results of experiments in which rats were fed with formulations comprising Urolithin A and either saline or a variety of other components such as medium-chain triglycerides and the level of the Urolithin A in the blood was assessed.

Blood was collected from the rats by jugular vein cannulation at different time points, and urolithin A was quantified in the plasma to determine its pharmacokinetic profile in the different formulations. Study of each formulation was repeated on six rats in total. FIG. 1 shows the resulting pharmacokinetic profiles of each of the formulations used. The data collected is summarised below in Table 3.

TABLE 3

Results of bioavailability study

| Parameter | Saline | 65 | 66 | 67 | 68 |
|---|---|---|---|---|---|
| $C_{max}$ (ng/ml) | 3.417 | 3.177 | 7.670 | 2.130 | 1.606 |
| Relative $C_{max}$ (% of formulation 66 $C_{max}$) | 44.5% | 41.3% | 100% | 27.7% | 20.9% |
| $T_{max}$ (h) | 24 | 4 | 4 | 4 | 4 |
| AUC | 29.97 | 28.77 | 51.49 | 20.04 | 15.70 |
| Relative bioavailibilty (% AUC of formulation 66) | 58.20% | 55.87% | 100% | 38.92% | 30.49% |

The suspension of urolithin A in saline shows a double-peak curve, with a considerably delayed $T_{max}$ value of 24 h, as well as a smaller peak in blood level at 4 h. In contrast, each of the formulations 65-68 comprising excipients display only a single peak, with a $T_{max}$ of 4 h. The single-peak pharmacokinetic profiles of formulations 65-68 are far more favourable for oral administration than the double-peak displayed by the saline suspension, as they facilitate optimization of dosing and frequency of administration.

As shown in Table 3 and FIG. 1, urolithin A when formulated with medium-chain triglycerides (formulations 65 and 66) is also more bioavailable than the formulation which does not comprise medium-chain triglycerides (formulation 67 and 68), as shown by the higher $C_{max}$ and AUC values. Formulation 66, which contains both medium-chain triglycerides and lecithin in combination, has a considerably greater $C_{max}$ and AUC, and the urolithin A of this formulation is more bioavailable than in the formulation which only contains lecithin and no medium-chain triglyceride (formulation 67), the addition of Tween 60 to the lecithin formulation, does not improve the bioavailability (formulation 68). The main difference in the formulations 65 and 68, were the substitution of lecithin for medium-chain triglycerides. The use of medium-chain triglycerides led to an increase of $C_{max}$ (ng/ml) from 1.606 in formulation 68 to 3.177 in formulation 65, or an increase of about 98%. Also, formulation 65 showed and AUC of 28.77 versus formulation 68 which had an AUC of 15.7, demonstrating an increase in bioavailability of 83% when medium-chain triglycerides are used in place of lecithin.

Formulations 65 and 66 according to the invention thus display both more favourable pharmacokinetic profiles, comprising only a single peak in blood concentration, as well as enhanced bioavailability, compared to unformulated urolithin in saline alone, rendering them useful in oral administration of urolithins.

Example 2: Comparison of the Pharmacokinetic Profile of Urolithin a in Formulation 66 in Both Rats and Humans The pharmacokinetic profile of urolithin A in formulation 66 in humans was compared to those observed in rats. An equivalent dose of urolithin A, as determined by surface area ratio between rats and human, was delivered in humans. Pharmacokinetic trials were performed with formulation 66 in rats at a dose of 60 mg/kg/d. The human equivalent dose, following FDA guidance on dose conversion based on surface ratio, is determined by dividing this dose by the conversion factor 6.2, resulting in a human equivalent dose of 9.68 mg/kg/d for a human. Assuming an average weight for an adult to be 60 to 70 kg, this would result in a daily dose of between 580 and 680 mg of urolithin A. Humans received a similar equivalent dose of 500 mg/day of urolithin A delivered in softgels. In both cases the urolithin A used in the formulations had a particle size distribution of $D_{90}$=81 μm to 20 μm and $D_{50}$=2 μm to 8 μm and a $D_{10}$=0.5 μm to 2 μm.

The pharmacokinetic profile for formulation 66 was determined in male Sprague-Dawley rats that were administered urolithin A in formulation 66 by oral gavage after overnight fasting, at a dose corresponding to 60 mg/kg/day. The components by % w/w of the formulations used are shown in Table 4 below.

TABLE 4

Formulation used in bioavailability study.

| Component | Formulation 66 |
| --- | --- |
| Urolithin A | 30.1 |
| Medium-chain triglycerides | 34.2 |
| Lecithin | 34.2 |
| Glycerol Monostearate | 1.4 |

The medium-chain triglycerides were obtained from Cremer Oleo GmbH & Co KG, under the product name CremerCOOR MCT 60/40 EP, which contains C6 ≤0.5%; C8 55-65%; C10 35-45%; and C12 ≤1.5%. The lecithin was obtained from Cargill, Inc., under the product name Epikuron® 135 F IP, which contains minimum 32% phosphatidylcholine.

The glycerol monostearate was obtained from Cremer Oleo GmbH & Co KG, under the product name IMWITOR® 900 (F) P, which contains 40.0-50.0% monoacylglycerols, 30.0-45.0% diacylglycerols, and 5.0-15.0% triacylglycerols.

Figure 2:
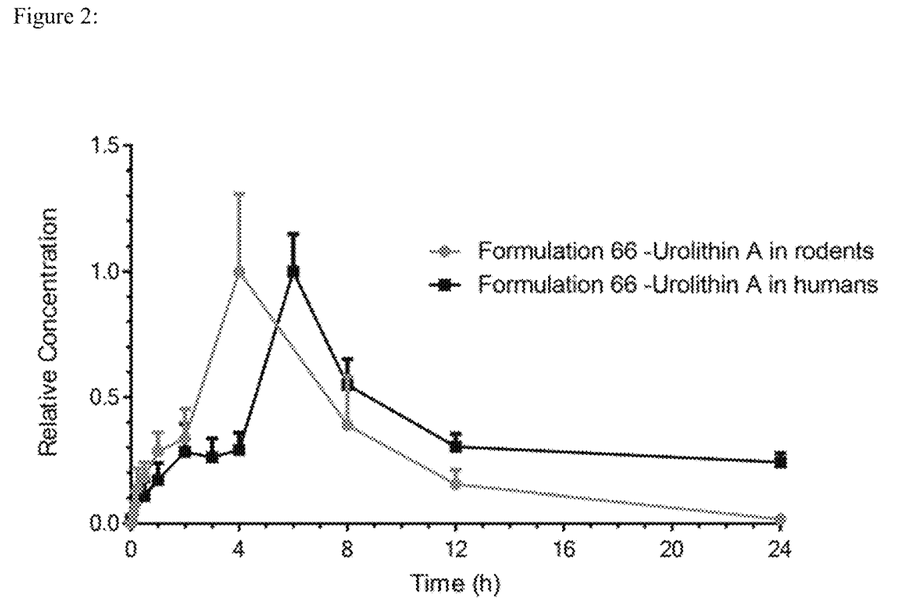
FIG. 2 shows the results of experiments in which rats and humans were fed with a formulation comprising Urolithin A and medium-chain triglycerides and the level of the Urolithin A in the blood was assessed.

Blood was collected from the rats by jugular vein cannulation at different time points, and urolithin A was quantified in the plasma to determine its pharmacokinetic profile. Study of the formulation was repeated in six rats in total. FIG. 2 shows the resulting pharmacokinetic profiles normalized to a relative $C_{max}$ of 1.

To compare the pharmacokinetic profiles in humans to that observed in rats at a dose of 60 mg/kg/d, softgel capsules containing 250 mg each of urolithin A in formulation 66 were prepared by standard methods.

To determine if the pharmacokinetic profile of urolithin A delivered by softgels containing formulation 66 was similar to that observed in rats, six healthy individuals, 3 males and 3 female adults were dosed with 500 mg of urolithin A delivered in two softgels. Individuals were fasted overnight and were administered orally at T0h, two softgels each containing 250 mg urolithin A in formulation 66, with water.

TABLE 5

Design of the bioavailability study.

| Test Article | Humans N = | Dose (mg) | Vehicle | Plasma Sampling Time Points |
| --- | --- | --- | --- | --- |
| Urolithin A | 6 | 500 mg | Formulation 66 in two softgels | Pre-dose, 0.5, 1, 2, 3, 4, 6, 8, 12, 24 and 36 hours |

Blood was sampled at the following time points: pre-dose, 0.5, 1, 2, 3, 4, 6. 8, 12, 24 and 36 hours. At each time point, a 6 mL blood sample was drawn into a K2-EDTA coated tube. The blood samples were inverted to completely mix with the anticoagulant. Within 30 minutes following blood collection, each blood sample was centrifuged at 1500 g for 10 minutes at 4° C. Within 30 minutes after the centrifugation, the top layer of human plasma was transferred into a pre-labelled polypropylene tube. The level of urolithin A was quantified in the plasma samples for each timepoint to determine its pharmacokinetic profile. FIG. 2 shows the resulting pharmacokinetic profile for formulation 66 in both rat and human samples. For the sake of comparison of these profiles, the maximum concentration found in the blood or Cmax was set to a value of 1.

As observed in FIG. 2, urolithin A delivered by softgel to humans displayed a similar pharmacokinetic profile as observed in rats, with a single rapid peak. The $T_{max}$ for rats was 4 h for rodents and 6 h for humans. This shift in the curve is likely due to the difference in administration of formulation 66, either by simple gavage in rodents or by softgels in humans. Also, in humans we see a sustained level of urolithin A in the blood that was not anticipated from the rodent data, further highlighting the usefulness of medium-chain triglycerides in the oral delivery of urolithins to humans.

This shows that the formulation 66, containing medium-chain triglycerides, is useful for delivering urolithin A in humans and other mammals. These results demonstrate that urolithin A when formulated in formulation 66 containing MCT's displays an attractive bioavailability profile in both humans and rats and shows a favorable pharmacokinetic profile, rendering them useful in oral administration of urolithins.

Example 3: Effects of Particle Size on Urolithin a Bioavailability

The particle size of urolithin A was reduced in a controlled manner using an MC50 Spiral Jetmill, using filtered nitrogen, with a feed rate of 240 g/hr, a Venturi pressure of 12 bar, and a mill pressure of 12 bar. Different particle size distributions of urolithin A were determined on a Malvern Particle Size analyzer (Malvern Instruments, UK). Three samples were evaluated in depth. Sample #1 of urolithin A had a particle size distribution of $D_{10}$ of 1.03 µm, a $D_{50}$ of 53.4 µm and a $D_{90}$ of 365 µm. Sample #2 of urolithin A had a particle size of $D_{10}$ of 0.272 µm, a $D_{50}$ of 2.17 µm and a $D_{90}$ of 6.84 µm. Sample #3 of urolithin A had a particle size of $D_{10}$ of 0.597 µm, a $D_{50}$ of 5.67 µm and a $D_{90}$ of 40.1 µm

TABLE 6

Particle size determinations for urolithin A before and after micronization

| Urolithin A | $D_{10}$ | $D_{50}$ | $D_{90}$ |
|---|---|---|---|
| Sample #1 | 1.03 µm | 53.4 µm | 365 µm |
| Sample #2 | 0.272 µm | 2.17 µm | 6.84 µm |
| Sample #3 | 0.597 µm | 5.67 µm | 40.1 µm |

To demonstrate the impact of particular particle size distributions on bioavailability, male Sprague-Dawley rats were fasted overnight and then administered by oral gavage with either sample #1, sample #2, or sample #3 of urolithin A suspended in 15% DMSO, 85% (0.5% methyl cellulose, 0.25% Tween 80 in Water), at a dose corresponding to 25 mg/kg/day.

TABLE 7

Design of the bioavailability study.

| Test Article | Animals N= | Dose (mg/kg) | Dosing Solution Conc. (mg/mL) | Dosing Volume (mL/kg) | Vehicle | Plasma Sampling Time Points |
|---|---|---|---|---|---|---|
| Urolithin A Sample #1 | 3 | 25 | 5 | 5 | 15% DMSO 85% (0.5% methyl cellulose/0.25% Tween 80 in Water) | Pre-dose, 0.25, 0.5, 1, 2, 4, 8, 12, 24 and 48 hours |
| Urolithin A Sample #2 | 3 | 25 | 5 | 5 | 15% DMSO 85% (0.5% methyl cellulose/0.25% Tween 80 in Water) | Pre-dose, 0.25, 0.5, 1, 2, 4, 8, 12, 24 and 48 hours |
| Urolithin A Sample #3 | 3 | 25 | 5 | 5 | 15% DMSO 85% (0.5% methyl cellulose/0.25% Tween 80 in Water) | Pre-dose, 0.25, 0.5, 1, 2, 4, 8, 12, 24 and 48 hours |

The solutions for gavage were prepared as follows: 35 mg of urolithin A powder was diluted in 7 ml of 15% DMSO, 0.5% methyl cellulose/0.25% Tween 80 in water, resulting in a 5 mg/ml fine suspension. The DMSO was obtained from BDH, methyl cellulose was obtained from Sigma, and Tween 80 was obtained from Sigma-Aldrich.

Figure 3:
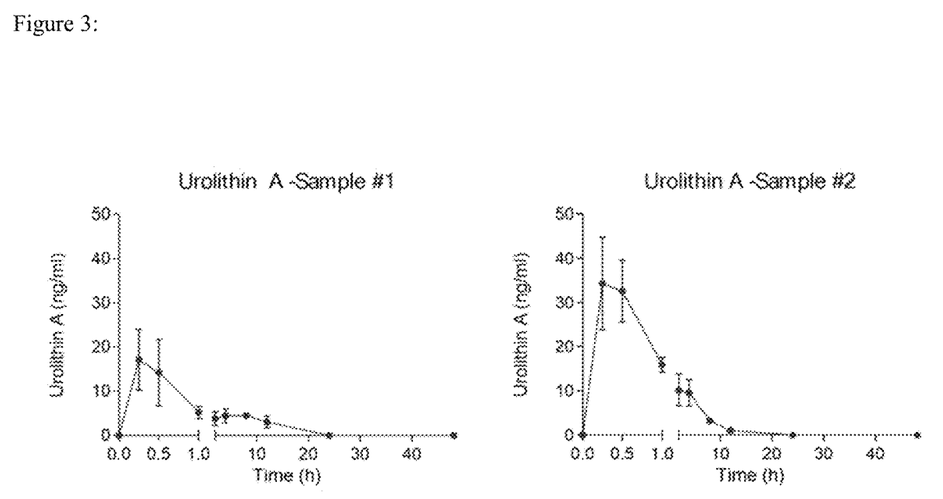
FIG. 3 shows the results of experiments in which rats were fed with formulations comprising Urolithin A at a variety of different particle sizes and the level of the Urolithin A in the blood was assessed.

Blood was collected from the rats by jugular vein cannulation at different time points, and urolithin A was quantified in the plasma to determine its pharmacokinetic profile following oral gavage of Sample #1, Sample #2, and Sample #3. The study was repeated on three rats for each sample. FIG. 3 shows the resulting pharmacokinetic profiles of urolithin sample #1 and sample #2. The data collected is summarized below in Table 8.

TABLE 8

Results of bioavailability study for urolithin A with different particle sizes

| Paramter | Sample #1 | Sample #2 | Sample #3 |
|---|---|---|---|
| $C_{max}$ (ng/ml) | 17.1 | 37 | 17.4 |
| Relative $C_{max}$ (% of non-micronized $C_{max}$) | 100% | 216% | 102% |
| $T_{max}$ (h) | 0.25 | 0.33 | 0.50 |
| AUC | 75.1 | 96.2 | 94.8 |
| Relative bioavailability (% AUC of non-micronized urolithin A) | 100% | 128% | 126% |

Urolithin A showed an increase in bioavailability when particle size was reduced below a $D_{90}$ of 50 µm. For Sample #2 there was a relative increase in the Cmax of 116% (2.16-fold increase) and an increase in the AUC of 28%, in comparison to Sample #1. For Sample #3 there was a relative increase in the AUC of 26%.

These results demonstrate that urolithin A preparations having a particle size of $D_{90}$<50 µm consistently shows a higher bioavailability when compared to urolithin A preparations having a particle size of $D_{90}$>300 µm. Additionally, it was observed that urolithin A preparations having particle size of $D_{90}$<20 µm were especially advantageous and enabled achieving dramatically higher peak urolithin A blood levels as the Cmax achieved more than doubled.

The invention claimed is:

1. A composition comprising:
   a) medium-chain triglyceride; wherein the medium-chain triglyceride constitutes 30-80% w/w of the composition;
   b) micronized urolithin A, having a $D_{50}$ size in a range of 0.5 to 50 μm, and a $D_{90}$ size in a range of 5 to 100 μm; and
   c) lecithin, wherein the lecithin constitutes 1-40% w/w of the composition;
   wherein the composition is formulated for oral administration.

2. The composition of claim 1, wherein the weight ratio between the medium-chain triglyceride component and the urolithin is in the range of 0.5:1 to 3:1.

3. The composition of claim 1, wherein the medium-chain triglyceride comprises calprylic acid or capric acid.

4. The composition of claim 3, wherein the medium-chain triglyceride is derived from a source selected from coconut oil, palm oil, and dairy fat.

5. The composition of claim 1, further comprising a stabiliser.

6. The composition of claim 5, wherein the stabiliser is glycerol monostearate.

7. The composition of claim 1, wherein the composition is a solid, a semi-solid, or a liquid.

8. The composition of claim 7, wherein the composition is in the form of a softgel.

9. The composition of claim 1, wherein the micronized urolithin A has a $D_{10}$ size in a range of 0.5 to 1.0 μm, the $D_{90}$ size in the range of 8.2 to 16.0 μm, and the $D_{50}$ size in the range of 2.8 to 5.5 μm.

* * * * *